US008124139B2

(12) United States Patent
Yie et al.

(10) Patent No.: US 8,124,139 B2
(45) Date of Patent: Feb. 28, 2012

(54) COMPOUND PREPARATION FOR QUICKLY REDUCING OXIDATIVE STRESS AND PREPARATION OF THE SAME

(75) Inventors: Hongping Yie, Huaibei (CN); Meg M. Sun, San Diego, CA (US); Zuolin Zhu, San Diego, CA (US); Wei Sun, Huaibei (CN); Zhongquan Zhao, Huaibei (CN); Jinyuan Wang, Huaibei (CN); Feng Zheng, Huaibei (CN)

(73) Assignee: Sino-US Pficker Pharmaceuticals Co., Ltd., Huaibei (CN)

( * ) Notice: Subject to any disclaimer, the term of this patent is extended or adjusted under 35 U.S.C. 154(b) by 195 days.

(21) Appl. No.: 12/441,485

(22) PCT Filed: Apr. 23, 2007

(86) PCT No.: PCT/CN2007/001335

§ 371 (c)(1), (2), (4) Date: May 8, 2009

(87) PCT Pub. No.: WO2008/034316

PCT Pub. Date: Mar. 27, 2008

(65) Prior Publication Data

US 2010/0015115 A1 Jan. 21, 2010

(30) Foreign Application Priority Data

Sep. 14, 2006 (CN) .......................... 2006 1 0153977

(51) Int. Cl.
*A61K 36/268* (2006.01)
*A61K 36/634* (2006.01)
*A61K 36/28* (2006.01)
*A61K 36/00* (2006.01)

(52) U.S. Cl. .......... 424/725; 424/756; 424/737; 426/73; 426/72

(58) Field of Classification Search ........................ None
See application file for complete search history.

(56) References Cited

U.S. PATENT DOCUMENTS

| | | | | |
|---|---|---|---|---|
| 6,013,623 A * | 1/2000 | Spector et al. | ............... | 424/94.4 |
| 2003/0108624 A1 * | 6/2003 | Kosbab | ......................... | 424/729 |

FOREIGN PATENT DOCUMENTS

| | | | |
|---|---|---|---|
| CN | 1093528 A | | 10/1994 |
| CN | 1620919 A | | 6/2005 |
| CN | 1686191 A | | 10/2005 |
| CN | 1742935 A | | 3/2006 |
| DE | 202005007462 | * | 8/2005 |

OTHER PUBLICATIONS

Goad, M. Home Remedies; Suffering Mainers Seek Cold Comfort From Concoctions Both Straightforward and Strange; Portland Press Hearald, Portland, Me.: Jan. 23, 2005, p. G1 (pp. 1-5 of ProQuest Database print-out).*

Langer, S. MotherYourself With Cold & Flu Remedies; Better Nutrition for Today's Living; Atlanta, Dec. 1995, vol. 57, Issue 12, p. 38 (pp. 1-3 of ProQuest Database print-out).*

Schwarcz, J. The Science of Chicken Soup and the Common Cold: Your Cold Will Disappear Within a Week. Guaranteed. Difficult Cases May Take Seven Days; The Spectator, Hamilton, Ontario, Feb. 28, 1998, p. W13 (pp. 1-3 of ProQuest Database print-out).*

Stapleton et al. Host Defense—A Role for the Amino Acid Taurine? Journal of Parenteral and Enteral Nutrition; Jan./Feb. 1998; 22, 1, pp. 42-48).*

Taste of Home Community; Does *Echinacea* Go Bad?; online, blog, URL<http://community.tasteofhome.com/forums/t/229412.aspx> 2003, pp. 1-6.*

Wotapka, D. 'Airborne' May Ease Cold Symptoms; Newsday; Long Island, N.Y.; Dec. 16, 2003 p. A43 (pp. 1-3 of ProQuest Database print-out).*

Balch et al. Presecription for Nutritional Healing, A-to-Z Guide to Supplements; Avery Publishing Group, Garden City Park, New York (1998) pp. 9-12 and 51-52.*

International Search Report of PCT/CN2007/001335, dated Aug. 2, 2007.

Wang et al. "Medical Plant in Europe and America." Chinese Wild Plant Resources, vol. 22(3), Jun. 2003, pp. 56-57.

Bursell et al. "The Potential Use of Glutathionyl Hemoglobin as a Clinical Marker of Oxidative Stress." Clinical Chemistry, vol. 46(2), 2000, pp. 145-146.

Van Remmen et al. "Oxidative damage to mitochondria and aging." Experimental Gerontology, 36, 2001, pp. 957-968.

* cited by examiner

*Primary Examiner* — Patricia Leith

(74) *Attorney, Agent, or Firm* — Hamre, Schumann, Mueller & Larson, P.C.

(57) ABSTRACT

The present invention discloses a compound preparation for quickly reducing oxidative stress, which contains small molecules and mineral trace elements that can remove or help removing free radicals, can regulate the function of endocrine and circulatory digestive system, as well as other components that can rebuild inner harmony. The compound preparation is in solid dosage form, preferably effervescent tablet or effervescent granules. The preparative method of the compound preparation is also disclosed. Animal experiment and clinical trial show that the invention has strong effect in reducing oxidative stress and disease prevention.

9 Claims, No Drawings

COMPOUND PREPARATION FOR QUICKLY REDUCING OXIDATIVE STRESS AND PREPARATION OF THE SAME

FIELD OF THE INVENTION

The present invention relates to pharmaceutical fields, especially relates to compound preparation for quickly reducing the oxidative stress and its preparation method.

BACKGROUND ARTS

Oxidative stress (OS) is caused by one or more reasons which disturb the balance between strong oxidant and antioxidant within the body, and the imbalance between strong oxidant and antioxidant is the main reason of a variety of cell injury within the body. Oxidative stress is considered as the primary reason for diabetes and chronic complications of diabetes, pulmonary fibrosis, epilepsy, hypertension, atherosclerosis and related cardiovascular diseases, cancer, kidney disease, and Parkinson's disease, etc (Clinical Chemistry, 2000, 46, 145-146). Oxidative stress may be involved in changing gene expression directly thereby result in the abnormal mechanism and eventually the lesion. Alternatively, oxidative stress may be involved in changing gene expression indirectly via some oxidized material. First of all, increased oxidative stress brings the body into a "sub-healthy" state, then into organic lesions. The period from oxidative stress increased above normal level to the appearance of organic lesions is known as the window period for oxidative stress attenuating intervention (WPOS). Within WPOS, the occurrence of various diseases can be effectively prevented by quickly reducing the oxidative stress level, i.e. by WPOS manipulation.

"Sub-health" refers to the body is between health and disease, there is no organic lesion in this state but has functional change. If the "sub-healthy" state is treated properly, then the body can be transformed to health; otherwise will be onset of disease. "Sub-health" is often diagnosed as fatigue syndrome, endocrine disorders, neurasthenia, and menopausal syndrome, etc. It is mainly represented as physical fatigue, fatigue, reduced immunity, easy to get cold, shortness of breath when sport, sweating, back and leg pain, anorexia and so on. The psychological specific appearance include hypoemotivity, emotional low, the reaction retardation, insomnia and more dreams, daytime sleepiness, inattention, memory loss, irritability, anxiety, easily frightened and so on. The "sub-healthy" population is more prone to be ill than health population. And the person engaged in mental labor is in high-risk of "sub-health".

The main reason for "sub-healthy" is broken down from constant overwork, including physiological and psychological overload. Besides the physiological overload caused by excess exercise, mental overload is more easily to induce oxidative stress increasing and reduced immunity, which is an important reason for sub-health and is a threat of life. Secondly, lack of exercise is also a very important inducement. Due to lack of time to do physical exercises, there will be disorders of cardio- and cerebro-vascular, gastrointestinal system, immune system, as well as the areas of cervical disease. Thirdly, the working environment is of significant impact. For instance, prolonged use of computer will result in vision recession, joint injury, radiation injury, head and shoulder pain, as well as autonomic nervous system disorders, depression, arteriosclerotic psychosis. Finally, environmental factors are also of great importance. Air pollution, automobile exhaust pollution do harm on our body, at the same time, long-term use of food additives, clenbuterol and antibiotics will damage health.

In order to avoid "sub-healthy" state by means of reducing the oxidative stress slowly, one should change their life pattern, have reasonable meals, sleep adequately and on schedule, and exercise appropriately. Meanwhile, one should learn how to regulate his emotion, to treat pressure, to open mind, and to cultivate a wide range of interests and hobbies. Also, if possible, try best to improve the environmental conditions.

It is very important and necessary to use exogenous means to reduce the oxidative stress rapidly. First, many people are too busy to do enough physical exercise; second, the amount of materials secreted by the body have a limit to against oxidative stress, especially with the aging of the body, the number of free radicals generated by the body rise rapidly (Exp Gerontol, 2001, 36, 957-968), and the synergy effect between the materials against excessive free radicals also declined greatly. The above methods such as do physical exercise and change life style can not quickly reduce oxidative stress, and when oxidative stress levels are very high the body's immune ability is very low and are in high risk of ill.

Therefore, the materials and methods for rapidly reducing oxidative stress is in urgent need.

SUMMARY OF THE INVENTION

The subject of the present invention is to provide a composition to quickly reduce oxidative stress and the preparation and use thereof.

In the first aspect, the invention provides a compound preparation for quickly reducing oxidative stress, the compound preparation contains:

small molecule compounds and mineral elements, which can remove all kinds of free radicals (from aqueous and lipid phase) quickly;

components to regulate the function of endocrine and circulatory digestive system.

In a preferred embodiment, the compound preparation for quickly reducing oxidative stress contain:

(a) small molecule organic compounds, the small molecule organic compounds including:
  - (a1) vitamin A, vitamin B2, L-lysine HC1, and L-glutamine;
  - (a2) one of the three substances such as vitamin C, glutathione and folic acid, or combinations thereof; and
  - (a3) one of the four substances such as vitamin E, coenzyme Q10, lutein, and lycopene, or combinations thereof;

(b) mineral trace elements: zinc, selenium, manganese, magnesium and potassium;

(c) herbal ingredients: *Lonicera, Schizonepeta*, Ginger, Chinese vitex, *Forsythia, Echinacea, Isatis* root;

(d) maltodextrin; and (e) a pharmaceutically acceptable carrier.

In a preferred embodiment, the dosage of each component described in (a), (b), (c) and (d) in a single dose of the compound preparation is:

Vitamin A is in the range from 1000 international units (IU) to 6000 international units (IU), vitamin B2 is in the range from 0.1 mg to 10 mg, vitamin C is in the range from 10 mg to 2000 mg, glutathione is in the range from 50 mg to 1500 mg, folic acid is in the range from 50 μg to 2000 μg, vitamin E is in the range from 10 international units (IU) to 2000 international units (IU), coenzyme Q10 is in the range from 1.0 mg to 1000 mg, lutein is in the range from 0.1 mg to 100 mg, lycopene is in the range from 0.1 mg to 300 mg, L-lysine HC1 is in the range from 1.0 mg to 1000 mg, L-glutamine is in the range from 1.0 mg to 1000 mg;

Zinc is in the range from 1.0 mg to 100 mg, magnesium is in the range from 1.0 mg to 300 mg, manganese is in the range from 0.1 mg to 100 mg, selenium is in the range from 1.0 μg to 300 μg, potassium is in the range from 1.0 mg to 1000 mg;

*Lonicera, Schizonepeta*, Ginger, Chinese vitex, *Forsythia, Echinacea, Isatis* root can be original grass or be extracts thereof, wherein, *Lonicera*, based on chlorogenic acid, is in the range from 0.1 mg to 100 mg, *Schizonepeta*, based on *Schizonepeta* volatile oil, is in the range from 10 μg to 20 mg, Ginger, based on gingerols, is in the range from 10 μg to 50 mg, Chinese vitex, based on polysaccharide, is in the range from 10 μg to 100 mg, *Forsythia*, based on Forsythin, is in the range from 1 μg to 2 mg, *Echinacea*, based on phenolic resin, is in the range from 1-10 mg, *Isatis* root, based on indirubin, is in the range from 0.001 μg to 10 μg;

The maltodextrin is in the range from 0.1 mg to 200 mg.

In a preferred embodiment, the dosage of each component described in (a), (b), (c) and (d) in a single dose of the compound preparation is:

Vitamin A is in the range from 3000 international units to 5000 international units, vitamin B2 is in the range from 0.5 mg to 5 mg, vitamin C is in the range from 50 mg to 1500 mg, folic acid is in the range from 100 μg to 1000 μg, vitamin E is in the range from 15 international units to 1000 international units, coenzyme Q10 is in the range from 5.0 mg to 800 mg, lutein is in the range from 0.2 mg to 80 mg, lycopene is in the range from 0.3 mg to 200 mg, L-lysine HC1 is in the range from 1.0 mg to 1000 mg, L-glutamine is in the range from 1.0 mg to 1000 mg;

Selenium is in the range from 5 μg to 280 μg.

In a preferred embodiment, the dosage of each component described in (a), (b), (c) and (d) in a single dose of the compound preparation is:

Vitamin A is in the range from 4500 international units to 5000 international units, vitamin B2 is in the range from 1.0 mg to 3.2 mg, vitamin C is in the range from 100 mg to 1100 mg, folic acid is in the range from 200 μg to 900 μg, vitamin E is in the range from 20 international units to 100 international units, coenzyme Q10 is in the range from 40 mg to 400 mg, lutein is in the range from 0.5 mg to 30 mg, lycopene is in the range from 0.4 mg to 100 mg, L-lysine HC1 is in the range from 1.0 mg to 1000 mg, L-glutamine is in the range from 1.0 mg to 1000 mg;

Selenium is in the range from 10 μg to 100 μg.

In a preferred embodiment, a single dose of the compound preparation for quickly reducing oxidative stress also contains Taurine, and/or lipoic acid; the Taurine is in the range from 50 mg to 1500 mg, the lipoic acid is in the range from 1.0 mg to 3000 mg.

In a preferred embodiment, a single dose of the compound preparation for quickly reducing oxidative stress also contains pharmaceutically acceptable mineral oil, which is in the range from 10 mg to 100 mg.

In a preferred embodiment, the compound preparation for quickly reducing oxidative stress is in solid dosage form.

In a preferred embodiment, the solid dosage form of the compound preparation for quickly reducing oxidative stress is effervescent tablet or effervescent granules.

In the second aspect, the invention provides the method to prepare the compound preparation for quickly reducing oxidative stress, the method contains the steps of:

Mixing (a) small molecule compounds, wherein the small molecule compounds including:

(a1) vitamin A, vitamin B2, L-lysine HC1, and L-glutamine;

(a2) one of the three substances such as vitamin C, glutathione and folic acid, or combinations thereof; and (a3) one of the four substances such as vitamin E, coenzyme Q10, lutein, and lycopene, or combinations thereof;

(b) mineral trace elements: zinc, selenium, manganese, magnesium and potassium;

(c) herbal ingredients: *Lonicera, Schizonepeta*, Ginger, Chinese vitex, *Forsythia, Echinacea, Isatis* root;

(d) maltodextrin; and (e) a pharmaceutically acceptable carrier, to get the compound preparation.

In a preferred embodiment, the compound preparation is in form of effervescent granules or effervescent tablet, and its preparation process contains the steps of:

(1) Pre-treatment: crushing, screening and drying the active components such as small molecule organic compounds and mineral trace elements;

(2) Mixture: the above mentioned active components are weighted according to the above formulation, mixing thoroughly with effervescent base, effervescent acid, flavoring agents, glidant and lubricant for 5-15 min in a general mixture equipment then adding with herbal ingredients and maltodextrin and mixing thoroughly;

(3) Dry granulation: At 15-25° and relative humidity about 10%, compressing the mixed powder by dry granulation machine, then breaking into effervescent granules;

(4) compressing the effervescent granule into effervescent tablet.

In a preferred embodiment, the effervescent granules or the effervescent tablet is prepared by:

A) drying, crushing and screening the components; B) weighing and mixing thoroughly; C) adding with lubricant and granulated; D) adding with acid-base effervescent components and mixing into effervescent granules; E) compressing into effervescent tablet; F) packaging.

In the third aspect, the invention provides the use of the compound preparation, wherein the compound preparation is used as oxidative stress controller or used in the manufacture of a medicine to prevent or treat oxidative stress.

In the forth aspect, the invention provides the method of controlling oxidative stress, which includes the step of administering an effective amount of composition to the subject in need of, wherein the composition contains:

(a) small molecule organic compounds, the small molecule organic compounds including:

(a1) vitamin A, vitamin B2, L-lysine HC1, and L-glutamine;

(a2) one of the three substances such as vitamin C, glutathione and folic acid, or combinations thereof; and (a3) one of the four substances such as vitamin E, coenzyme Q10, lutein, and lycopene, or combinations thereof;

(b) mineral trace elements: zinc, selenium, manganese, magnesium and potassium;

(c) herbal ingredients: *Lonicera, Schizonepeta*, Ginger, Chinese vitex, *Forsythia, Echinacea, Isatis* root;

(d) maltodextrin.

In the fifth aspect, the invention provides the method of treating diseases related with oxidative stress, which includes the step of administering an effective amount of composition to the subject in need of, wherein the composition contains:

(a) small molecule organic compounds, the small molecule organic compounds including:

(a1) vitamin A, vitamin B2, L-lysine HC1, and L-glutamine;

(a2) one of the three substances such as vitamin C, glutathione and folic acid, or combinations thereof; and (a3) one of the four substances such as vitamin E, coenzyme Q10, lutein, and lycopene, or combinations thereof;

(b) mineral trace elements: zinc, selenium, manganese, magnesium and potassium;

(c) herbal ingredients: *Lonicera, Schizonepeta*, Ginger, Chinese vitex, *Forsythia, Echinacea, Isatis* root;

(d) maltodextrin.

Accordingly, the present invention provides the material and method of rapidly reducing oxidative stress.

DETAILED DESCRIPTION OF THE INVENTION

Through extensive and intensive study, the inventors unexpectedly discovered a composition which can effectively and quickly reduce the oxidative stress. The composition contains small molecule organic compounds, mineral trace elements, herbal medicines, maltodextrin and so on. The small molecule organic compound is selected from the group consisting of vitamin A, vitamin B2, L-lysine HC1, L-glutamine, compound to remove free radicals from aqueous phase, compound to remove free radicals from lipid phase, and so on; mineral trace elements are selected from the group consisting of zinc, selenium, manganese, magnesium, and potassium, and so on; herbal medicines selected from the group consisting of *Lonicera, Schizonepeta*, Ginger, Chinese vitex, *Forsythia, Echinacea*, and *Isatis* root, and so on.

Definitions

The term "containing" or "including" as used herein refers to "comprising", "substantially consisting of" and "consisting of".

The term "substantially consisting of" as used herein refers to besides the necessary components in the composition, there also contains small amounts of minor components and/or impurities without affecting the active components. For example, sweeteners to improve tasty, fragrances to improve odor, as well as other additives commonly used in this field.

The term "effective dosage" as used herein refers to an amount which has function of activity on human and/or animals and can be accepted by human and/or animals.

The term "pharmaceutically or bromatologically acceptable carrier" as used herein refers to a carrier used in the medicine or health food, including a variety of excipients and diluents. The term refers to a number of carriers: they are not necessary active ingredients per se, and do not have toxicity after administration. Suitable vectors are known to those skilled in the art. The review of a pharmaceutically acceptable excipients can be found in Remington's Pharmaceutical Sciences (Mack Pub. Co., N.J. 1991). The pharmaceutically acceptable carrier includes liquid, such as water, saline, glycerol and ethanol. In addition, these carriers also includes adjuvant, such as wetting agent or emulsifier, pH buffer substances. Non-essential components other than vitamin A, vitamin B2, L-lysine HC1, L-glutamine, compounds to remove free radical from aqueous phase, L-lysine HC1, compounds to remove free radical from lipid phase; zinc, selenium, manganese, magnesium, potassium, and maltodextrin, as well as raw material or extract from *Lonicera, Schizonepeta*, Ginger, Chinese vitex, *Forsythia, Echinacea* and *Isatis* root, and other non-essential components (such as other auxiliary medical material or food material), also include in the definition of pharmaceutically or bromatologically acceptable carrier.

The term "necessary component" as used herein refers to the necessary chemical substances used as active ingredient, i.e. L-lysine HC1, L-glutamine, compounds to remove free radicals from aqueous phase, compounds to remove free radicals from lipid phase, zinc, selenium, manganese, magnesium, potassium, and maltodextrin, as well as original raw material or extract from *Lonicera, Schizonepeta*, Ginger, Chinese vitex, *Forsythia, Echinacea* and *Isatis* root. More preferably, including vitamin A, vitamin B2 and so on.

The term "composition of the invention" as used herein refers to pharmaceutical compositions, food compositions, health care product compositions, and/or dietary additives, as long as they contain or substantially consist of the following substances: L-lysine HC1, L-glutamine, compounds to remove free radicals from aqueous phase, compounds to remove free radicals from lipid, zinc, selenium, manganese, magnesium, potassium, and maltodextrin, as well as original plants or extract of *Lonicera, Schizonepeta*, Ginger, Chinese vitex, *Forsythia, Echinacea* and *Isatis* root. More preferably, including vitamin A, vitamin B2 and so on.

"To reduce oxidative stress" or "oxidative stress controller" as used herein refers to the compositions which can rapid remove of excess free radicals, reduce or control the occurrence of oxidative stress, protecting the body from oxidative damage and improve the health status of the body.

The term "unit dosage form" or "single dose" as used herein refers to the composition of the invention is formulated into required single dosage form for facility, including, but not limited to, a variety of solid dosage form, such as tablets, capsules and sustained release dosage form. The "unit dosage form" or "single dose" contains the composition of the invention which can reduce or control oxidative stress effectively, thus prevent, treat, or improve sub-health state or diseases caused by oxidative stress.

Active Ingredient

Since sub-health state caused by increased oxidative stress has a plurality of performance and relates to the function of many body systems, there is in need of active components that play role in most body organs and enhance immunity. The main materials used to against oxidative stress include both small molecular compounds such as vitamin E, vitamin C, and lipoic acid, etc.; and trace elements such as zinc, vanadium, and selenium, etc.; also include macromolecular proteins, such as glutathione peroxidase(GPx), catalase, superoxide dismutase(SOD), glutathione reductase(GR) and so on. But for macromolecular protein antioxidants, such as glutathione peroxidase, catalase, superoxide dismutase, and glutathione reductase, etc., injection should be used to achieve desired effect among the existing delivery methods. But this method is inconvenient, uncomfortable, and high cost, oral administration is an ideal method. There are a lot of oral-delivery material, such as a series antioxidants as vitamin C, vitamin E, and lipoic acid, trace element selenium (Se) and zinc (Zn), a variety of amino acids such as L-lysine HC1 and so on. Chinese herbal medicine has some components that can clear heat & resolve toxin, regulating the metabolism, one of its main functions is to reduce oxidative stress, improve immunity, such as *Lonicera, Isatis* root and so on.

The compound preparation of the present invention can palliate symptoms and heal the disease. The guideline of the invention is, in the window period for oxidative stress attenuating intervention (WPOS), using novel compound preparation to effective interference the body thereby quickly lower the oxidative stress, wherein the compound preparation mainly contains two types of active ingredients: the first is small molecule compounds and mineral elements, which can rapid remove of all kinds of free radicals (from aqueous phase and lipid phase), the second is the components which can regulate the function of endocrine and circulatory digestive system. All of the active ingredients in the compound preparation of the invention active synergetically to achieve the purpose of prevention, every single component does not have the effect of the present product.

Small molecule compounds including vitamin A, vitamin B2, vitamin. C, vitamin E, L-lysine HC1, lipoic acid, L-glutamine, coenzyme Q10, glutathione, Taurine, lutein, folic acid, and lycopene and so on. The active components with similar functions should not all be appeared in the formula. For example, any of vitamin C, glutathione, and folic acid can remove free radicals from aqueous phase; any of vitamin A, vitamin E, coenzyme Q10, lutein, and lycopene can remove free radicals from lipid phase; lipoic acid can remove free radicals from both aqueous phase and lipid phase. If the formula contains vitamin C, then there is no need to add glutathione and folic acid, etc.; likewise, if the formula contains vitamin E, then there is no need to add coenzyme Q10, lutein, and lycopene, etc.; and if the formula contains vitamin C and vitamin E, then there is no need to add lipoic acid.

This is the same for mineral trace elements and herbal ingredients of clear heat & resolve toxin and regulating the metabolism. The mineral trace elements according to the invention including the components of removing free radicals and regulating the function of endocrine and circulatory digestive system, such as zinc, selenium, manganese, magnesium, and vanadium, potassium, etc.; the herbal ingredients according to the invention includes all of the components which have the function of clear heat & resolve toxin and regulating the metabolism, such as *Lonicera, Schizonepeta*, Ginger, Chinese vitex, *Forsythia, Echinacea*, and *Isatis* root, etc., also includes maltodextrin.

The active ingredients of the invention include, but not limited to, those listed above.

One or more active ingredients with similar function can exist in a single dose of the invention simultaneously. If only have one active ingredient, its amount in a single dose is as follow:

Small Molecule Compounds:

vitamin A is in the range from 1000 international units (IU) to 6000 international units (IU), more preferably from 3000 international units to 5000 international units, and most preferably from 4500 international units to 5000 international units;

vitamin B2 is in the range from 0.1 mg to 10 mg, more preferably from 0.5 mg to 5 mg, and most preferably from 1.0 mg to 3.2 mg;

vitamin C is in the range from 10 mg to 2000 mg, more preferably from 50 mg to 1500 mg, and most preferably from 100 mg to 1100 mg;

vitamin E is in the range from 10 international units (IU) to 2000 international units (IU), more preferably from 15 international units to 1000 international units, and most preferably from 20 international units to 100 international units;

lutein is in the range from 0.1 mg to 100 mg, more preferably from 0.2 mg to 80 mg, and most preferably from 0.5 mg to 30 mg;

folic acid is also a kind of vitamin B group, it is in the range from 50 μg to 2000 μg, more preferably from 100 μg to 1000 μg, and most preferably from 200 μg to 900 μg;

lipoic acid is in the range from 1.0 mg to 3000 mg, more preferably from 5.0 mg to 1200 mg, and most preferably from 40 mg to 700 mg; alternatively, the effective amount of lipoic acid is from 1.0 mg/kg body weight to 200 mg/kg body weight, more preferably from 1.2 mg/kg body weight to 70 mg/kg body weight;

lycopene is in the range from 0.1 mg to 300 mg, more preferably from 0.3 mg to 200 mg, and most preferably from 0.4 mg to 100 mg;

coenzyme Q10 is in the range from 1.0 mg to 1000 mg, more preferably from 5.0 mg to 800 mg, and most preferably from 40 mg to 400 mg.

glutathione is in the range from 50 mg to 1500 mg;

Taurine is in the range from 50 mg to 1500 mg;

L-lysine HC1 is in the range from 1.0 mg to 1000 mg;

L-glutamine is in the range from 1.0 mg to 1000 mg;

mineral element:

zinc is in the range from 1.0 mg to 100 mg;

magnesium is in the range from 1.0 mg to 300 mg;

manganese is in the range from 0.1 mg to 100 mg;

potassium is in the range from 1.0 mg to 1000 mg;

selenium is in the range from 1.0 μg to 300 μg, more preferably from 5 μg to 280 μg, and most preferably from 10 μg to 100 μg;

herbal ingredients:

*Echinacea* original grass or concentrated liquid extract, based on phenolic resin, is in the range from 1-10 mg;

*Lonicera* original grass or concentrated liquid extract, based on chlorogenic acid, is in the range from 0.1 mg to 100 mg;

*Schizonepeta* original grass or concentrated liquid extract, based on *Schizonepeta* volatile oil, is in the range from 10 μg to 20 mg;

Ginger original grass or concentrated liquid extract, based on gingerols, is in the range from 10 μg to 50 mg;

Chinese vitex original grass or concentrated liquid extract, based on polysaccharide, is in the range from 10 μg to 100 mg;

*Forsythia* original grass or concentrated liquid extract, based on Forsythin, is in the range from 1 μg to 2 mg;

*Isatis* root original grass or concentrated liquid extract, based on indirubin, is in the range from 0.001 μg to 10 μg;

Moreover:

Maltodextrin is in the range from 0.1 mg to 200 mg.

Since constipation is common in the population with high oxidative stress, the stool softeners such as pharmaceutically acceptable mineral oil can be added, and is in the range from 10 mg to 100 mg.

The separate explanations of the mechanisms of the above mentioned active ingredients are as following.

Vitamin B2 Vitamin B2 is a component of flavoprotein cofactor, when lacking, the biology oxidation process of the body will be effected and result in dysbolism. Its common symptoms are inflammation in mouth, eyes and genitalia, such as angular cheilitis, cheilitis, glossitis, conjunctivitis and oscheitis.

Vitamin A Vitamin A has many physiological functions, it is necessary in the development of vision, growth, epithelial tissue and bone, sperm production and fetal growth and development, it is mainly used to improve vision and enhance the immune system. Vitamin A is a general name, which includes retinol, carotenoid, carotene, and retinoid, carotenoid and carotene can be transformed into vitamin A by the body. They can effectively phagocytose free radicals and reduce oxidative stress, and they can inhibit a lot of carcinogens.

Glutathione (L-glutamyl-L-cysteinyl-glycine), which exists in all animal cells and presents as its reduced form (GSH) under normal circumstances. Glutathione is the major intracellular non-protein mercapto-compound. Glutathione has many direct or indirect effects on living body, including regulation of gene expression, enzyme activity and metabolic regulation, protection of cells, transport of amino acid, regulation of immune function, and so on. Oxidative stress or electrophilic compound attacking can decrease intracellular GSH content, or turn it into an oxidized disulfide (GSSG). Glutathione is primarily as detoxification, antioxidant drugs in clinical.

Lipoic acid Lipoic acid is a natural antioxidant in the body, and is produced by mitochondria. It can increase the concentration of water-soluble vitamin C and fat-soluble vitamin E inside and outside the cell simultaneously, and can regenerate vitamin C and vitamin E via the redox property of lipoic acid. Lipoic acid is a substitute of other antioxidants. In other words, if vitamin E or C is deficiency in the body, lipoic acid will in place of them. The antioxidant effect of lipoic acid is better than vitamin A, C, E. Lipoic acid can eliminate free radicals which accelerate aging and cause disease, and maybe is one of the strongest natural antioxidants currently known.

*Echinacea* In the past two or three decades, in view of modern medicine, numerous clinical trials prove that *Echinacea* has a good therapeutic effect and drug safety, wherein including the effect on innate immune system deficiency disease. In modern medicine, the use of *Echinacea* focused on its effects on immune system, and mainly on the treatment of viral infection. It is proved through more than 3900 clinical trials that the juice of *Echinacea* can well decrease the incidence of cold and influenza, relief the symptoms and so on. Also found that the juice of *Echinacea* can effectively inhibit virus proliferation, control virus replication. *Echinacea* can stimulate non-specific defense mechanisms, attack virus infected cells.

Vitamin E Vitamin E can promote the absorption, use and liver storage of vitamin A. Because of the structure characteristic and body distribution of vitamin E, it has a series of functions of anti-free radical, anti-aging, liver protection and liver cell regeneration, enhance immunity, and the protection of cardiovascular and skin. Vitamin E is high efficiency against free radical lipid peroxidation. It is found in the study that lack of vitamin E will affect the immune function of both human and animal, resulting in not only lower humoral immunity but also cell-mediated immunity.

Lutein Lutein is the most important nutrient in human retina. The eye retina macula lutea (central vision) and the crystalline lens both contain high levels of lutein. Lutein has been proven to be an important natural antioxidant. Hawaii Cancer Center found that lutein is one of the most effective ingredients of inhibiting lipid peroxidation occurred in blood and eyes. Lutein can resist these damages after free radicals oxidation, especially in the retina and crystalline lens region in the eye.

Lycopene Lycopene is a kind of antioxidant, which will be resinificated to form lycopene epoxide (an epoxide of lycopene) and increase of 40% after contacting with oxygen. Lycopene is the strongest antioxidant as for the removal of fat-soluble free radicals in the body. Lycopene can inhibit the production of lipid peroxide, can prevent adult diseases, including prevent cardiovascular disease and prostate or digestive tract cancer, inhibit colorectal cancer and bladder cancer, prevent hypertension, lower blood fat, against cell damage, protect human DNA, proteins, fats and lipids, and so on.

Coenzyme Q10 Coenzyme Q10 is synthesized in the liver with tyrosine, phenylalanine, vitamin E, B1, B6 and folic acid. The various effects of coenzyme Q10 including the protection of heart and blood vessels, which is the most important one, have been or are being continuously found. Coenzyme Q10 mainly exists in the heart, liver, kidney, and pancreas in the body. Its important functions include regulation of cell growth and maintenance of cell, as well as antioxidation. Coenzyme Q10, an antioxidant, can reduce the damage of free radicals to the cells of these organs, thereby protect the heart, liver, kidney, and pancreas and other vital organs. The free radical damage on the cells in these organs includes DNA damage.

Vitamin C Vitamin C is an essential vitamin for human and is thought of playing an important role in the redox. The formation and maintenance of intercellular matrix and collagen, the conversion of folic acid and tyrosine metabolism are all in require of vitamin C. Vitamin C is an essential antioxidant for tissue growth and repair of health gingival, which can promote blood circulation, allaying tiredness, improve white blood cell function, enhance immunity, prevent scurvy, prevent fractures and so on, and can lower cholesterol and high blood pressure, prevention arteriosclerosis, protect the liver and liver detoxification.

Folic acid Folic acid naturally presents in animal liver and kidney. Folic acid is a water-soluble B vitamin consisting of pteridine, p-amino benzoic acid and glutamic acid residue. Folic acid is an essential material for the body cell growth and reproduction. Folic acid is a water-soluble vitamin assisting the mature of red blood cell. Folic acid is often associated with liver preparations to treat pernicious anemia, and is indispensable for the manufacture of red blood cell.

Taurine Taurine is present in the human body. Scientific research confirms that, taurine is widely distributed in heart, liver, gastrointestinal tract, pancreas, central nervous system, eyes and other organs and tissues. The function of taurine is to protect heart, lower blood pressure, lower blood fat, lower blood sugar, reduce the fatty liver, lower transaminase, enhance immunity, anti-fatigue, and so on. Taurine is an essential nutrient for human health.

Glutamine Glutamine has many functions on human body, including the followings: glutamine is the most common and essential amino acid in human body, accounting for 60% of the total amino acids weight; the key element for maintaining muscle metabolism and structure; the basic fuel and energy source for immune system; requirement of deoxyribonucleic acid (DNA) synthesis, cell differentiation and growth, as well as wound healing and tissue repairing; the basic nutrient for gastrointestinal epithelial cell; toxin neutralization.

Lysine Lysine is an essential amino acid, which can not be synthesized by the body and is called the first deficiency amino acid in nutriology. Lysine is of great important for human protein synthesis and development, which can improve human digestion and absorption capacity, speed up protein synthesis, and provide basic material for growth and development. The person will be in partial eclipse, choosy in food, anorexia, and even apastia when lacking of lysine, thereby result in slow growth or stop growth, shorter than the people of the same age, bone calcification slow and so on.

Zinc Zinc mainly present in the bone, skin, and hair, which involves in more than 50 enzymes and plays important role in nucleic acid metabolism and in protein synthesis. Furthermore, zinc is an antioxidant and is a component of insulin. Zinc is in close relation to genital function and is an essential element to promoting human growth and development. Deficiency of zinc can cause growth retardation and adverse wound healing and, especially in infants and young children, impact growth in stature.

Selenium During the last twenty years, selenium is found to have significant impact on human health. Selenium can not only improve the human immune system with anti-cancer effect, but also be able to maintain body tissues young, reduce the pains from pathogenic fire impairment, inflammation and scald, and reduce the suffering of menopause. If the body lack of selenium, male sexual function will decrease early. Selenium is very important for the liver. Modern medicine research has proven the theory of traditional Chinese medicine compound. For example, clinical trials found that vitamin E and selenium are two synergistic substances, and have stronger effects when taking simultaneously than taking separately.

Magnesium Magnesium is also an important component for bones and teeth. It mainly complexes with proteins and can maintain a normal heart rhythm, inhibit nerve excitability, involve in protein synthesis, muscle contraction and body temperature regulation. Magnesium deficiency will induce decline of spirits, muscle weakness, tetany, tachycardia and, in young children, also induce convulsion. Also, Magnesium is anti-oxidant.

Manganese Manganese is a coenzyme, which is needed for many biochemical reactions in human body. Manganese deficiency results in fatigue or fatigue syndrome, energy deficiency, which is because the enzyme is involved in energy metabolism and the final aim of energy metabolism is to release energy. Energy deficiency will induce a lot of phenomena: fatigue, lethargy, listlessness and so on. The combination of Manganese and vitamin B group is especially good to enhance the person's mental state.

Maltodextrin Maltodextrin is produced from refined corn starch by enzymatic hydrolysis, which is a product between starch and starch sugar, and has the advantages of strong thickener, good carrier, poor fermentation capacity, easy to digest and absorb, low sweetness, low-calorie, low fat and so on. It is identified in pathology that, long-term intake of dextrin has no side effects, and can promote normal body metabolism and has some preventive effects on hypertension, obesity, especially diabetes, dental, etc.

*Lonicera* The pharmaceutically acceptable part of *Lonicera* is the dried flower, stems and leaves. The flower is clear heat & resolve toxin. The stems and leaves are heat-clearing and antirheumatic, and can treat cold, pneumonia, etc., which is the component of Five Flowers Tea, *Lonicerae* and *Forsythiae* Antiphlogistic Pill.

*Forsythia Forsythia* is the dried fruit of *Oleaceae Forsythia. Forsythia* has the function of clear heat & resolve toxin, detumescence and eliminating stagnation, and is one of the commonly-used medicines. The main active ingredient of *Forsythia* is volatile oil, which mainly present in the center of *Forsythia* and with the content of 4% or above, average of 3.8%, a plant with such a high oil content is rare in the nature. In the past literatures it is thought that the *Forsythia* volatile oil has significant and stable anti-bacterial and anti-viral effects.

*Schizonepeta Schizonepeta* is the dried aerial parts of *Labiatae Schizonepeta*, which is pungent, microtherm, expelling wind with diaphoresis, and can be used to treat rubella and mineral pyocutaneous disease.

Ginger Ginger can alleviate cold symptoms and so on. Ginger is rich of antioxidant components, which can effectively adjust the digestive system, alleviate diarrhea resulting from improper diet. Studies also show that, some components of ginger can also lower the absorption of cholesterol in vessel and liver, help to enhance cardiac function, adjuvant therapy of coronary cardiovascular disease. In addition, the ginger extract is used to treat migraine, dizziness, vomiting, improve gastrointestinal function, dyskinesia and arthritis, and enhance immunity.

Chinese vitex Chinese vitex is a Verbenaceae plant, and is a variant of Vitex. Its fruit is used in medicine and has the effect of invigorating stomach to relieve phlegm.

*Isatis* root *Isatis* root is heat-clearing and detoxicating, which is used to treat viral colds, sore throat.

Other functional components can also include tea, hawthorn, ginkgo flavonoids, licorice flavonoid, and so on.

Compound Preparation

Besides the above mentioned active ingredients, the present invention also contains a pharmaceutically acceptable carrier.

The excipients used in the present invention contain the following: corn starch, used as filler and disintegrating agent; cellulose gel and pregelatinized starch, used as plasticizer and binder; gelatin, used as emulsifier, binder and disintegrating agent; glycerin, used as flavoring agent; hydroxypropyl cellulose, used as aqueous dispersing agent; magnesium/zinc stearate, talc, silica, and mineral oil, which are used as lubricant; microcellulose, used as binder and disintegrating agent; croscarmellose sodium, used as binder and disintegrating agent; lactose, used as filler and binder; acacia, used as emulsifier and binder; stearic acid, used as emulsifier and binder; hydrdxypropyl methylcellulose, used as binder and disintegrating agent; sorbitol, sucralose, acesulfame potassium, and sugar, which are as flavoring agent; polyethylene glycol, used as filler, emulsifier, and disintegrating agent; modified food starch, used as filler and disintegrating agent; as well as soybean oil and lecithin and so on, which are as lipid soluble auxiliary material; sorbitol, used as binder, and titanium dioxide, used as coloring agent, etc.

The compound preparation of the invention is a solid dosage form, such as tablet, granule, pill, and capsule, etc., preferably is effervescent tablet or effervescent granules. Effervescent tablet or effervescent granules can rapidly disintegrate in water, so that the active ingredients is quickly released, the physiological activity of the active ingredients is fully maintained, the stability of bioactive substances is improved, thereby promote the body to rapidly absorb the active ingredients, enhance the stability of bioactive ingredients, speed up absorption by human body, and easy to use. The effervescent tablet or effervescent granules can be added with orange, strawberry, lemon flavor.

The solid dosage forms of the present invention can be produced using various known manufacturing processes. Both effervescent granules and effervescent tablet can be produced with conventional production processes. The process is, first, the compatible active ingredients, lipids or fat-soluble auxiliary substances, and one or more excipients are mixed into a mixture, into which is added other ingredients and excipients, mix thoroughly to get homogeneous mixture.

A preferred method is:

1. Using original plants, or prepared extract powder, or directly preparing the commercial extract products of the selected herbal medicine in proportion;

2. Mixture: Each of the active components are crushed, screened, dried as required, then weighted according to the formulation. The effervescent base, effervescent acid, flavoring agent, glidant and lubricant are added into general mixer, mixing for 5-15 min to mixed thoroughly, then the product of step 1 is added and mixed thoroughly.

3. Dry granulation: At 15-25° C., relative humidity of about 10%, using dry granulation machine, the mixed powder is compressed, broken into particles to get effervescent granules.

4. Tabletting: At 15-25° C., relative humidity of about 10%, using 2-3 cm diameter dies, compressed in a tabletting machine to get effervescent tablets. Each tablet has the weight of 2.5-8 grams, preferably 3-6 grams.

In another preferred embodiment, the method is:

1. Each component is dried, crushed and screened;
2. Weighting and mixing thoroughly;
3. Adding lubricant and granulating;
4. Adding effervescent acid-base components, then mixing;
5. Tabletting;
6. Packaging.

All the active components of the present invention are commercial available products. Herbal ingredients can be original herbal powder, or can be extract powder. Extract powder is produced as follows:

Equivalent (weight ratio) of *Lonicera, Schizonepeta*, Ginger, Chinese vitex, *Echinacea, Isatis* root, and *Forsythia* is weighted, boiling with water to get extract, dissolving in alcohol, concentrating, spray-drying into powder. The result extract powder has ≦3.5% water, and with the fineness of all can through 100 mesh. The active ingredients in the extract powder is, based on the dry weight of the weighted herbal, chlorogenic acid ($C_{16}H_{18}O_9$) not less than 0.3%, phenolic compounds not less than 0.8%, volatile oil not less than 0.10% (ml/g), and at the same time galuteolin ($C_{21}H_{20}O_{11}$), piperitone ($C_{10}H_{16}O$), 6-zingiberol, potassium myronate, indican, and forsythin ($C_{29}H_{36}O_{15}$) can be detected.

The effervescent agent in the effervescent granules or effervescent tablet consists of acidifying agent and edible alkalizing agent which can produce carbon dioxide. Effervescent agent weights 25%-60% (wt) of the effervescent tablet.

Effervescent base is a mixture of potassium and sodium carbonate, or a combination of bicarbonate, or a mixture of carbonate and bicarbonate, the acceptable carbonate and bicarbonate may include sodium bicarbonate, potassium bicarbonate, sodium carbonate, potassium carbonate, sodium glycinate carbonate, the preferred effervescent base is anhydrous potassium bicarbonate and sodium bicarbonate. In the present invention, effervescent base has the fineness of 60-200 mesh. Before use, the bicarbonate is dried for 2-4 hours at 60-80° C., and the carbonate is dried for 2-4 hours at 105-120° C.

Effervescent acids are edible organic acids, including one or two of citric acid, citrate glycine, citrate sodium, malic acid, tartaric acid, and fumaric acid, which have the fineness of 60-200 mesh, and should be dried for 2-4 hours at 105-110° C. before use.

Lubricant includes the inner lubricant and additive lubricant. The inner lubricant is the lubricant added into the material before granulating. The additive lubricant is added before tabletting of added in the mold during tabletting. The Lubricant includes one or two of polyethylene glycol 6000, fumaric acid, adipic acid, leucine, vegetable oil, or a pharmaceutically acceptable mineral oil, wherein leucine, vegetable oil, or a pharmaceutically acceptable mineral oil can be used as additive lubricant.

The invention use spray-drying technology combined with dry granulation process to prepare effervescent tablet, and use spray-drying technology to prepare herbal extracts. Spray drying method can be used to prepare extract powder with larger surface area, which can dissolve rapidly when be placed in water.

Use

The compound preparation of the invention can be used as oxidative stress controller, or used in the manufacture of a medicine to prevention or treatment of oxidative stress.

A piece of the effervescent tablet can be put into small amount of pure water, then to drink the solution about 3 minutes later when all dissolved. The administration frequency is about every three hours of even less, based on the specific circumstances and needs. When the formulation is produced to quickly lower the oxidative stress, due to the high level of the components used to capture free radicals in the compound preparation, if the tablet is taken every three hours, it is better not to use continuously more than three days.

The use of the effervescent granules and of the effervescent tablet is the same.

The daily oral dosage of other solid dosage forms, such as tablet, granule, pill and capsule, is similar to the effervescent tablet or effervescent granules. The accurate dosage for specific conditions depends on many factors, including weight, age, sex, symptoms, disease severity, route of administration and so on.

The compound preparation of the invention can rapidly reduce the oxidative stress so as to ensure human health, to improve work efficiency, to reduce medical costs, especially to meet the daily needs of mental workers, as well as to reduce a temporary high level of oxidative stress caused by a variety of reasons, such as job stress, mental stress, improve immunity, avoid illnesses caused by long-distance travel or going to restaurants, hospitals and other public places.

The above features or the features in following examples can be combined arbitrarily.

The following are the main advantages of the invention:

1. The compound preparation of the invention can rapidly reduce the oxidative stress;
2. The compound preparation of the invention can be effective in improving sub-health state;
3. The compound preparation of the invention can be effective in prevention and treatment of colds and influenza;
4. The compound preparation of the invention (effervescent tablet or effervescent granule) is easy to take.

The present invention has clinically proven the feasibility of window perиof for oxidative stress attenuating intervention (WPOS). The invention is further illustrated by the following examples. These examples are only intended to illustrate the invention, but not to limit the scope of the invention. For the experimental methods in the following examples, they are performed under routine conditions, or as instructed by the manufacturers, and all parts, percents, rations are by weight, unless otherwise specified.

Unless otherwise defined, all the professional and scientific terminologies used in the context have the common meaning known to the skilled person. In addition, all the methods and materials that similar with or equal to the disclosed invention can be used to practice the invention. The preferred examples and materials are only in way of illustration.

EXAMPLE 1-3

Compound Preparation Formulations 1-3
1. The components is shown in Table 1:

| | components | Formulation 1 (mg) | Formulation 2 (mg) | Formulation 3 (mg) |
|---|---|---|---|---|
| 1 | Vitamin A palmitate | 2.75 | 2.75 | 2.75 |
| 2 | vitamin C | 1000 | | |
| 3 | lipoic acid | | 1000 | 820 |
| 4 | folic acid | | 20 | |
| 5 | Taurine | | | 500 |
| 6 | Vitamin E acetate | 20 | | |
| 7 | Vitamin $B_2$ (Riboflavin) | 2.8 | 2.8 | 2.8 |
| 8 | Magnesium oxide | 66 | 66 | 66 |

-continued

| | Compound Preparation Formulations 1-3<br>1. The components is shown in Table 1: | | | |
|---|---|---|---|---|
| | components | Formulation 1 (mg) | Formulation 2 (mg) | Formulation 3 (mg) |
| 9 | Selenium (amino acid chelate) (Selenium >2%) | 0.75 | 0.75 | 0.75 |
| 10 | Manganese gluconate | 25 | 25 | 25 |
| 11 | maltodextrin | 43 | 43 | 43 |
| 12 | *Lonicera* | 43 | 43 | 43 |
| 13 | *Schizonepeta* | 43 | 43 | 43 |
| 14 | *Ginger* | 43 | 43 | 43 |
| 15 | Chinese *vitex* | 43 | 43 | 43 |
| 16 | *Isatis* root | 43 | 43 | 43 |
| 17 | *Echinacea* | 43 | 43 | 43 |
| 18 | *Forsythia* | 43 | 43 | 43 |
| 19 | Zinc sulfate monohydrate | 22 | 22 | 22 |
| 20 | L-lysine HCl | 25 | 25 | 25 |
| 21 | L-glutamine | 25 | 25 | 25 |
| 22 | Citric acid | 1567 | 1567 | 1567 |
| 23 | Sodium bicarbonate | 840 | 840 | 840 |
| 24 | Sorbitol | 473 | 473 | 473 |
| 25 | Potassium bicarbonate | 192 | 192 | 192 |
| 26 | Orange Flavor | 95 | 95 | 95 |
| 27 | Mineral oil | 26 | 26 | 26 |
| 28 | Sucralose | 2 | 2 | 2 |
| 29 | Acesulfame potassium | 2 | 2 | 2 |
| | Total Weight W = | 4730.3 | 4730.3 | 4730.3 |

(二) Preparation Methods:

1. Effervescent Granules:

The magnesium oxide (100-160° dried for 2-4 hours), manganese gluconate (105-110° dried for 2-4 hours), zinc sulfate monohydrate (165-190° dried for 2-4 hours), citric acid (105-110° dried for 2-4 hours), sodium bicarbonate, and potassium bicarbonate (60-80° dried for 2-4 hours) in Formulation 1 were dried, then crushed and screened;

The active components *Lonicera, Schizonepeta*, Ginger, maltodextrin, Chinese vitex, *Forsythia, Echinacea*, and *Isatis* root in Formulation 1 were mixed thoroughly to prepare the herbal powder;

The vitamin A, vitamin B2, vitamin C, vitamin E, L-lysine HC1, and L-glutamine in Formulation were weighed according to the Formulation 1;

The dried magnesium oxide, manganese gluconate, zinc sulfate monohydrate, and selenium (amino acid chelate) in Formulation 1 were weighed according to Formulation 1;

The sorbitol, orange flavor, sucralose, and acesulfame potassium in Formulation I were weighed according to Formulation 1;

The materials in step 2-5 were mixed with sprayed mineral oil in high speed mixture granulating machine to get granules;

The resultant granules were screened into general mixer, and mixed thoroughly with citric acid, sodium bicarbonate, potassium bicarbonate to get the mixture under 20% relative humidity;

Sealed the dampproof package under dry conditions.

2. Effervescent Tablet:

The resultant mixture from step 7, which was used to prepare granule, was compressed to shape in a tabletting machine using 2-3 cm diameter dies under 15-25° C. and 10% relative humidity, 1000 tablets were produced, each tablet weighed 4.73 grams, then sealed the dampproof package under dry conditions.

EXAMPLE 4-6

Animal Experiments

The effervescent tablet from Example 1-3 was used in animal experiments to test the effects of the three Formulations on oxidative stress. The test animals were four-weeks old nude mice, which were fed in standard animal experiment environment and ad libitum to water and food. The mice were divided into six groups, six mice per group. Group 1 was a blank control, receiving no X-ray irradiation. The mice of remaining groups each received 50 Gy whole body X-ray irradiation to increase their oxidative stress level. Group 2 and 3 received X-ray irradiation but without the effervescent tablet of the invention; group 4 was fed Formulation 1 effervescent tablet immediately after exposure to X-ray; group 5 was fed Formulation 2 effervescent tablet immediately after exposure to X-ray; group 6 was fed Formulation 3 effervescent tablet immediately after exposure to X-ray. The dose of effervescent tablet for test mice was 1 g/kg body weight for 4 times for every four hours. The skin tissue of the test mice was sampled at 36 and 72 hour after X-ray irradiation, each sample of about 50 mg was immediately frozen in liquid nitrogen and stored at −80° C.

TABLE II

| Oxidative stress level of test mice | | |
|---|---|---|
| | MAD(nmol/mg protein) | |
| | 36 h | 72 h |
| Group 1: Blank | 34.5 | 33.9 |
| Group 2: Irradiation | 60.3 | 71.2 |
| Group 3: Irradiation | 59.8 | 71.8 |
| Group 4: Formulation 1 | 35.4 | 34.8 |
| Group 5: Formulation 2 | 35.7 | 35.2 |
| Group 6: Formulation 3 | 35.2 | 34.9 |

The oxidative stress level in test mice was determined by the lipid oxidation product malondialdehyde (MDA) content in the skin sample, using Thiobarbituric Acid Reactive Substances [TBARS, Biochemical Analysis (Anal. Biochem.) 1979 , 95, 351-358], which measures organic phase absorbance at 532 nm. The calculated values are in Table II.

The results show that, the compound preparation of the invention is good at lowering the oxidative stress level.

EXAMPLE 7

Clinical Trial

The Formulation 1 effervescent tablet produced in example 1 was used in clinical trial. The clinical trial recruited 20 people, male, aging from 28-45 years old. The recruitment critical was, the people feel uncomfortable but without any diseases been detected. The 20 person were randomly divided into two groups, each group 10 persons. One group received orange flavor soluble corn starch effervescent tablet placebo, the other group received Formulation 1 effervescent tablet, 1 tablet at each time, every four hours once, and up to 11 times. Three days later, there were only one person with elevated body temperature and cold&flu symptom in Formulation 1 effervescent tablet group, and the number was 7 in placebo group.

The results show that, the compound preparation of the invention can quickly reduce oxidative stress and has good prevention effect on disease.

EXAMPLE 8-9

Clinical Trial

The clinical trial described in Example 7 is repeated using the Formulation 2, 3 effervescent tablet of Example 2-3. Monitoring the malondialdehyde concentration in the user. The results show that, the concentration of malondialdehyde, an oxidative stress marker, quickly reduced. This suggests that, the compound preparation of the invention can quickly reduce oxidative stress and has good prevention effect on oxidative stress related disease.

All the documents cited herein are incorporated into the invention as reference, as if each of them is individually incorporated. Further, it would be appreciated that, in the above teaching of invention, the skilled in the art could make certain changes or modifications to the invention, and these equivalents would still be within the scope of the invention defined by the appended claims of the application.

What is claimed is:

1. A compound preparation for reducing oxidative stress comprising:

vitamin A in the range from 1000 international units (IU) to 6000 international units,
vitamin B2 in the range from 0.1 mg to 10 mg,
vitamin C in the range from 10 mg to 2000 mg,
vitamin E in the range from 10 international units (IU) to 2000 international units,
folic acid in the range from 50 μg to 2000 μg,
coenzyme Q10 in the range from 1.0 mg to 1000 mg,
glutathione in the range from 50 mg to 1500 mg,
lutein in the range from 0.1 mg to 100 mg,
lycopene in the range from 0.1 mg to 300 mg,
L-lysine HC1 in the range from 1.0 mg to 1000 mg,
L-glutamine in the range from 1.0 mg to 1000 mg,
zinc in the range from 1.0 mg to 100 mg,
magnesium in the range from 1.0 mg to 300 mg,
manganese in the range from 0.1 mg to 100 mg,
selenium in the range from 1.0 μg to 300 μg,
potassium in the range from 1.0 mg to 1000 mg,
and maltodextrin in the range from 0.1 mg to 200 mg;
herbal extracts including:
Lonicera extract having chlorogenic acid,
Schizonepeta extract having Schizonepeta volatile oil,
Chinese vitex extract having polysaccharide,
Forsythia extract, having forsythin,
Isatis root extract having indirubin,
Ginger extract having gingerol, and
a pharmaceutically acceptable carrier.

2. The compound preparation of claim 1 further comprising taurine from 50 mg to 1500 mg and lipoic acid from 1.0 mg to 3000 mg.

3. The compound preparation of claim 1 further comprising pharmaceutically acceptable mineral oil from 10 mg to 100 mg.

4. The compound preparation of claim 1 wherein the compound preparation is in solid dosage form.

5. The compound preparation of claim 4, wherein the solid dosage form is an effervescent tablet or effervescent granules.

6. The compound preparation of claim 1 further comprising taurine from 50 mg to 1500 mg.

7. The compound preparation of claim 1 further comprising lipoic acid in the range from 1.0 mg to 3000 mg.

8. A method for reducing oxidative stress, said method comprising administering to a subject in need thereof, an effective amount of the composition according to claim 1.

9. A method of preparing the compound preparation of claim 1, wherein the method comprises mixing the following ingredients to prepare said preparation:

vitamin A in the range from 1000 international unit (IU) to 6000 international unit,
vitamin B2 in the range from 0.1 mg to 10 mg,
vitamin C in the range from 10 mg to 2000 mg,
vitamin E in the range from 10 international units (IU) to 2000 international units,
folic acid in the range from 50 μg to 2000 μg,
coenzyme Q10 in the range from 1.0 mg to 1000 mg,
glutathione in the range from 50 mg to 1500 mg,
lutein in the range from 0.1 mg to 100 mg,
lycopene in the range from 0.1 mg to 300 mg,
L-lysine HC1 in the range from 1.0 mg to 1000 mg,
L-glutamine in the range from 1.0 mg to 1000 mg,
zinc in the range from 1.0 mg to 100 mg,
magnesium in the range from 1.0 mg to 300 mg,
manganese in the range from 0.1 mg to 100 mg,
selenium in the range from 1.0 μg to 300 μg,
potassium in the range from 1.0 mg to 1000 mg,
and maltodextrin in the range from 0.1 mg to 200 mg;
herbal extracts including:
Lonicera extract having chlorogenic acid,
Schizonepeta extract having Schizonepeta volatile oil,
Chinese vitex extract having polysaccharide,
Forsythia extract, having forsythin,
Isatis root extract having indirubin,
Ginger extract having gingerol, and
a pharmaceutically acceptable carrier.

* * * * *